United States Patent
Grasmuck

(10) Patent No.: US 8,096,783 B2
(45) Date of Patent: Jan. 17, 2012

(54) APPARATUS FOR DELIVERING A REGULATED SUPPLY OF A GAS, PARTICULARLY RESPIRATORY ASSISTANCE APPARATUS

(75) Inventor: Gilbert Grasmuck, Toulouse (FR)

(73) Assignee: Air Liquide Medical Systems S.A., Antony (FR)

( * ) Notice: Subject to any disclaimer, the term of this patent is extended or adjusted under 35 U.S.C. 154(b) by 347 days.

(21) Appl. No.: 12/514,372

(22) PCT Filed: Nov. 12, 2007

(86) PCT No.: PCT/IB2007/003459
§ 371 (c)(1),
(2), (4) Date: May 11, 2009

(87) PCT Pub. No.: WO2008/059341
PCT Pub. Date: May 22, 2008

(65) Prior Publication Data
US 2010/0054969 A1    Mar. 4, 2010

Related U.S. Application Data

(60) Provisional application No. 60/937,075, filed on Jun. 25, 2007.

(30) Foreign Application Priority Data

Nov. 13, 2006   (FR) ..................................... 06 09886

(51) Int. Cl.
*F04D 29/58* (2006.01)
*F04D 25/08* (2006.01)

(52) U.S. Cl. ..................... 417/366; 417/423.8; 415/58.4
(58) Field of Classification Search .................. 417/371, 417/336, 423.8; 415/58.4, 101, 199, 116, 415/209
See application file for complete search history.

(56) References Cited

U.S. PATENT DOCUMENTS 5,560,075 A    10/1996    Jankowski
(Continued)

FOREIGN PATENT DOCUMENTS

EP    1 050 682    11/2000
(Continued)

OTHER PUBLICATIONS

International Search Report dated Apr. 9, 2008, from corresponding PCT application.

*Primary Examiner* — Karabi Guharay
*Assistant Examiner* — Elmito Breval
(74) *Attorney, Agent, or Firm* — Young & Thompson

(57) ABSTRACT

An apparatus (1) includes a housing (2), an air feed duct (21) a volute (5), an impeller (4), and a motor (3) for driving the rotation of the impeller (4) so as to generate a centrifugal air flow in the volute (5). The housing (2) has a first part (18a) where wall is intended, after assembly, to extend around the motor (3), espousing the shape of this motor (3) in such a way as to lie at a substantially constant distance from this motor (3); and a second part (18b, 19) where wall is intended, after assembly, to extend around the volute (5), espousing the shape of this volute (5) so as to lie at a substantially constant distance from this volute (5). The housing (2) internally forms a salient axial lump (20) which, after assembly, sits close to the hub (10) of the impeller (4).

19 Claims, 2 Drawing Sheets

U.S. PATENT DOCUMENTS

| | | | |
|---|---|---|---|
| 5,904,471 A * | 5/1999 | Woollenweber et al. | 417/371 |
| 6,439,861 B1 | 8/2002 | Shieh | |
| 2005/0053495 A1 | 3/2005 | Lebecq et al. | |
| 2006/0204361 A1 | 9/2006 | Xie | |
| 2008/0030087 A1 | 2/2008 | De Filippis et al. | |

FOREIGN PATENT DOCUMENTS

| | | |
|---|---|---|
| EP | 1 515 416 | 3/2005 |
| EP | 1 622 243 | 2/2006 |

* cited by examiner

APPARATUS FOR DELIVERING A REGULATED SUPPLY OF A GAS, PARTICULARLY RESPIRATORY ASSISTANCE APPARATUS

BACKGROUND OF THE INVENTION

1. Field of the Invention

The present invention relates to an apparatus for delivering a regulated supply of a gas, particularly to a respiratory assistance apparatus.

2. Description of the Related Art

It is known practice to produce respiratory assistance apparatus comprising a housing, an air feed duct delimited by the housing, a volute the inlet opening of which is in communication with the air feed duct, an impeller, situated immediately downstream of the inlet opening of the volute, comprising an inlet opening connected to this inlet opening of the volute and outlet orifices opening into the volute, and a motor for driving the rotation of the impeller.

The rotation of the impeller generates a centrifugal air flow which is converted into pressure in the volute.

SUMMARY OF THE INVENTION

This type of apparatus presents a significant problem concerning the cooling of the motor.

In an attempt to solve this problem, the idea has been had to fit the motor with a metallic mass that acts as a radiator. However, the performance obtained is not satisfactory, particularly when the gas flow rate is low.

The present invention aims to solve this essential problem, as best possible.

The apparatus to which the invention relates is of the aforementioned type, comprising a housing, an air feed duct delimited by the housing, a volute, the inlet opening of which is in communication with the air feed duct, an impeller, situated immediately downstream of the inlet opening of the volute, comprising an inlet opening connected to this inlet opening of the volute and outlet orifices opening into the volute, and a motor for driving the rotation of the impeller so as to generate a centrifugal air flow in the volute.

According to the invention, the housing has a part the wall of which is intended, after assembly, to extend around the motor, espousing the shape of this motor in such a way as to lie at a substantially constant distance from this motor, the housing and the motor thus between them delimiting a gas flow passage with a gas inlet orifice at the opposite end to the impeller;

the housing has a part the wall of which is intended, after assembly, to extend around the volute, espousing the shape of this volute so as to lie at a substantially constant distance from this volute, the housing and the volute thus between them delimiting a gas flow passage extending as far as the inlet opening of the volute; and the housing internally forms a salient axial lump which, after assembly, sits close to the hub of the impeller.

Thus, according to the invention, the housing substantially espouses the shape of the motor and of the volute, as far as the inlet opening thereof, and comprises an axial internal lump which sits close to the hub of the impeller; the assembly delimits gas flow passages which constitute the duct through which this gas flows. This duct extends over the entire circumference of the motor and of the volute and has a continuous configuration with no appreciable variation in cross section. This duct thus allows the gas to flow around the entire motor, undisturbed, and allows this motor to be cooled as best possible, by forced convection.

As a preference, the walls of the housing and of the volute delimiting said duct have rounded shapes to give the duct a substantially smooth and uniform configuration, that is to say without salient or re-entrant sharp corners, particularly at the base of the volute and at said lump.

The gas flow is thus as undisturbed as possible, and does not therefore generate undesirable noise.

As a preference, the gas inlet orifice extends over the entire periphery of the motor.

This orifice thus provides a wide inlet for gas into the gas supply duct without disturbing the flow, and quietly.

To the same ends, the housing is preferably flared in the manner of the bell of a trumpet at the gas inlet orifice into said duct.

BRIEF DESCRIPTION OF THE DRAWING FIGURES

The invention will be clearly understood and other features and advantages thereof will become apparent with reference to the attached diagrammatic drawing which, by way of non-limiting example, depicts one preferred embodiment of the apparatus to which the invention relates.

DETAILED DESCRIPTION OF THE INVENTION

Figure 1:
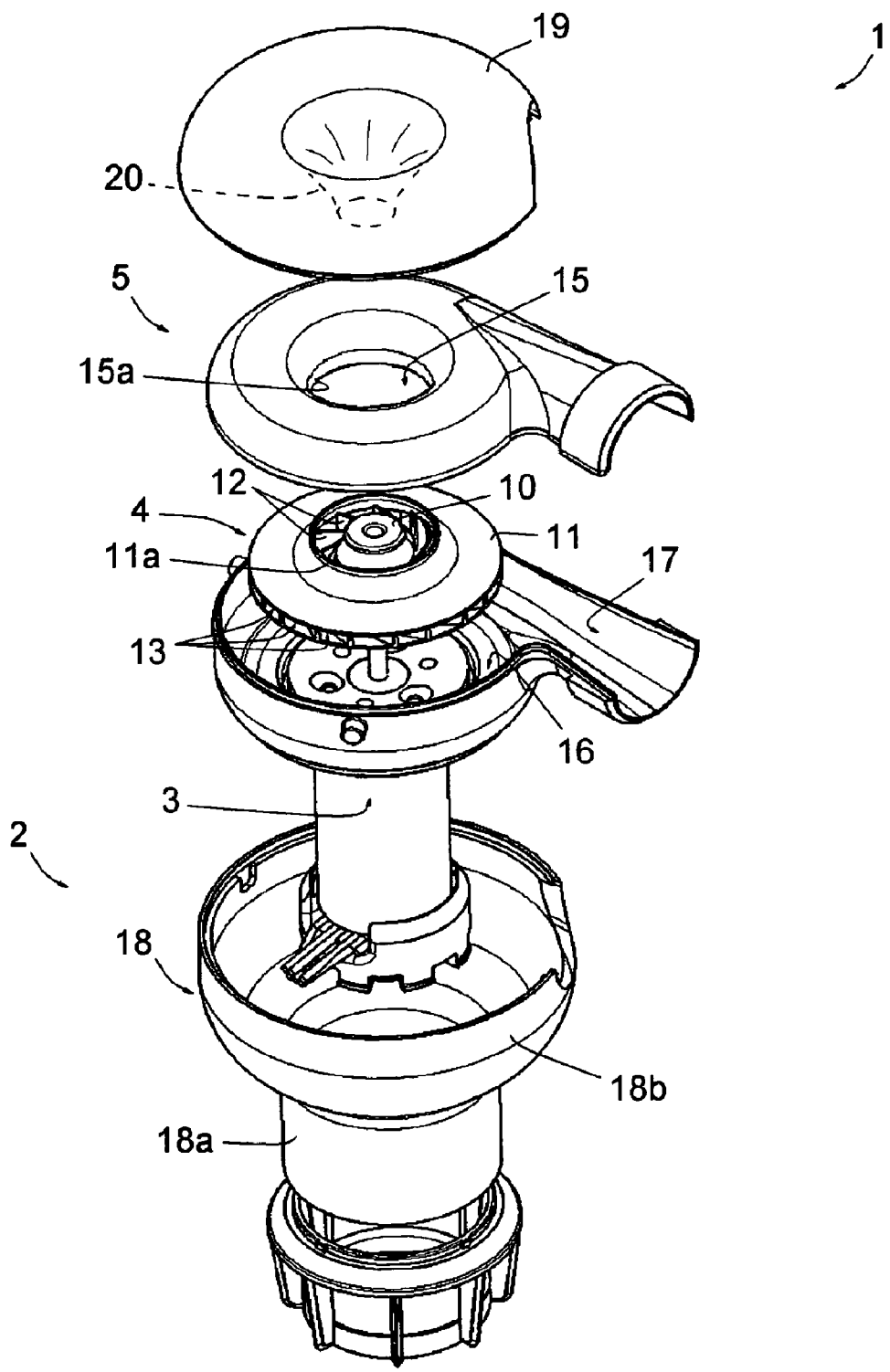
FIG. 1 is an exploded perspective view thereof.

The figures depict an apparatus 1 for delivering a regulated supply of a gas, particularly a respiratory assistance apparatus.

This apparatus 1 comprises a housing 2, a motor 3, an impeller 4 and volute 5.

The motor 3 has a cylindrical shape and comprises an output shaft to which the impeller 4 is secured. This motor 3 is axially connected to the volute 5 by means of screws (not depicted).

The impeller 4 comprises a hub 10, an upper wall 11 forming a turned-up rim 11a, vanes 12 extending from its middle towards its periphery and a lower wall. The hub 10 and the rim 11a between them delimit a circular air inlet opening. The vanes 12, together with the upper and lower walls of the impeller 4, delimit ducts 13 opening into/onto the periphery of the impeller 4, at the volute 5.

The rotation of the impeller 4 thus creates a centrifugal air flow which is converted into a pressure at the volute 5.

The volute 5 is formed of two shells which can be joined together. It comprises an air inlet opening 15, a hollow circular body 16 and an air outlet duct 17. The opening 15 is delimited by a rim 15a of the same diameter as the rim 11a and, after assembly, sits in close proximity to the latter. The volute 5 is positioned relative to the impeller 4 in such a way that the ducts 13 lie in the lower part of the body 16. The duct 17 is connected to downstream air-delivery members.

The housing 2 comprises a body 18 and a cover 19.

The body 18 comprises a circular lower part 18a and a flared upper part 18b that forms a rim to accept the cover 19. This body 18 is intended to house the motor 3 and the base part of the volute 5, and the cover 19 is intended to cover the upper part of the volute 5, for the duct 17.

The cover 19 forms an axial lump 20 projecting from its face that is intended to face the volute 5 and which, after assembly, sits near the hub 10 of the impeller 4.

Figure 2:
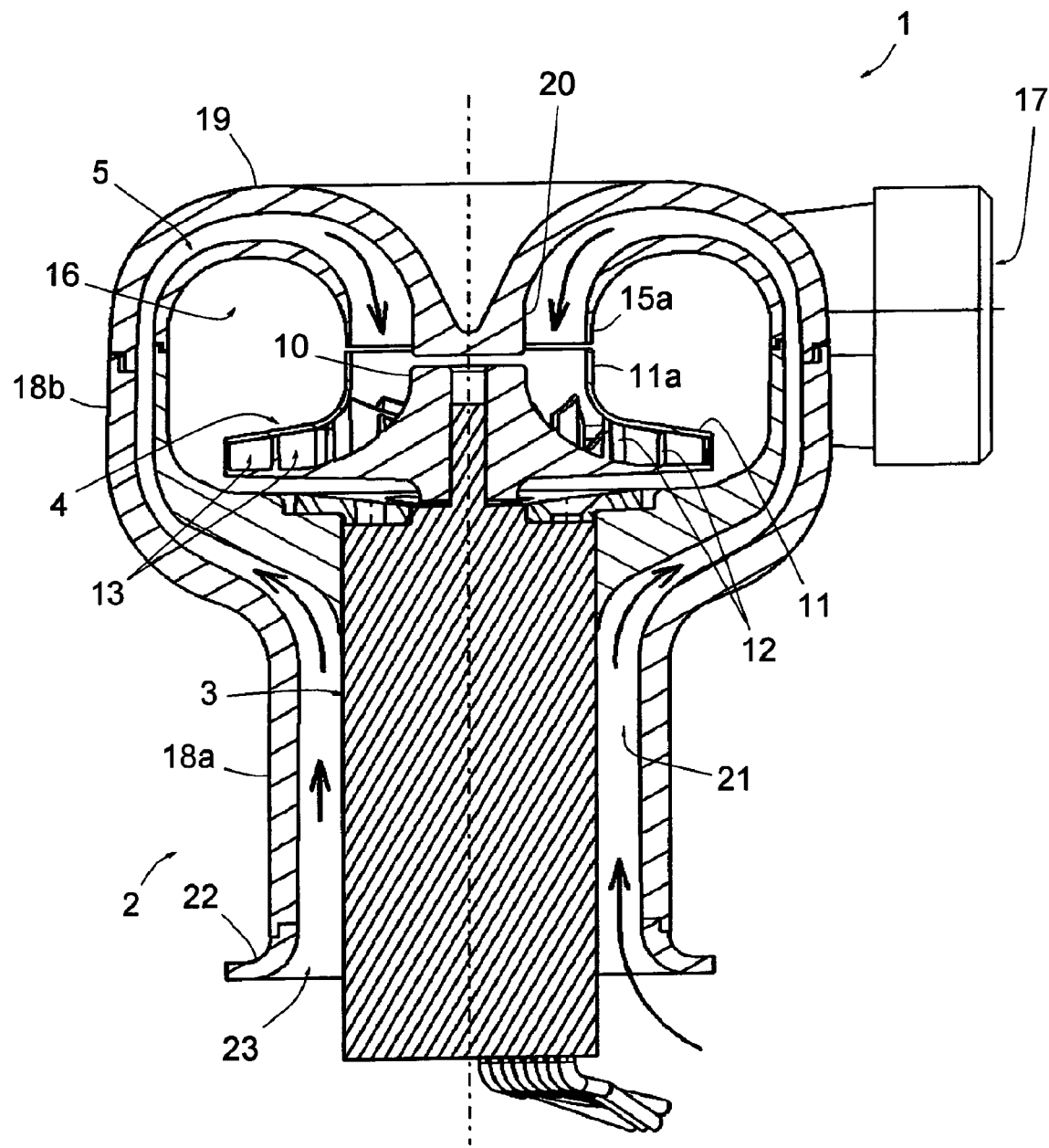
FIG. 2 is a view in axial section, on a plane substantially parallel to the axis of the outlet duct of the volute that this apparatus comprises.

As is particularly visible in FIG. 2, the wall of the part 18*a* extends, after assembly, around the motor 3 and is shaped to espouse the shape of this motor 3 so that it lies at a substantially constant distance therefrom; the walls of the part 18*b* and of the cover 19 extend, after assembly, around the volute 5 and are shaped to espouse the shape of this volute 5 such that they lie at a substantially constant distance from this volute 5. The housing 2, the motor 3 and the volute 5 thus between them delimit a gas flow duct 21 formed by the successive passages delimited by the wall of the part 18*a* and by the motor 3, by the wall of the part 18*b*, the wall of the cover 19 and by the volute 5 and by the lump 20 and the hub 10 of the impeller 4.

The duct 21 opens to the outside at the opposite end to the volute 5, over the entire periphery of the motor 3, and thus forms an air inlet orifice 22. The housing 2 may, at this orifice 22 and as shown by FIG. 2, have a flange 23 that is flared in the manner of the bell of a trumpet, which encourages the gas to enter without its flow being disturbed, and quietly.

FIG. 2 also shows that the walls of the housing 2 and of the volute 5 which delimit the duct 21 have rounded shapes giving this duct 21 a substantially smooth and uniform configuration, that is to say one with no salient or re-entrant sharp corners, particularly at the base of the volute 5 and at the lump 20.

As can be understood by reference to the figures, the housing 2 substantially espouses the shape of the motor 3 and of the volute 5, as far as the inlet opening thereof and delimits an airflow duct 21 which extends over the entire circumference of the motor 3 and of the volute 5 and which has a continuous configuration with no substantial variation in cross section. This duct 21 thus allows the gas to flow around the entire motor 3, undisturbed and forced, thus cooling this motor as best possible through forced convection.

The apparatus 1 thus solves the problem of the cooling of the motor 3, even if the gas flow rate is low.

It goes without saying that the invention is not restricted to the embodiment described hereinabove by way of example but that it extends to all embodiments covered by the claims appended hereto.

The invention claimed is:

1. An apparatus for delivering the regulated supply of a gas, comprising:
a housing;
an air feed duct delimited by the housing;
a volute, the volute having an inlet opening which is in communication with the air feed duct;
an impeller situated immediately downstream of the inlet opening of the volute, the impeller comprising an impeller inlet opening connected to this the inlet opening of the volute and outlet orifices opening into the volute; and
a motor configured for driving a rotation of the impeller so as to generate a centrifugal air flow in the volute, wherein:
the housing has a first part with a wall which is intended, after assembly, to extend around the motor, espousing a shape of the motor in such a way as to lie at a substantially constant distance from the motor, the housing and the motor between them delimiting a gas flow passage with a gas inlet orifice at an end opposite to the impeller;
the housing has a second part with a wall intended, after assembly, to extend around the volute, espousing a shape of the volute so as to lie at a substantially constant distance from the volute, the housing and the volute between them delimiting a gas flow passage extending as far as the inlet opening of the volute; and
the housing internally forms a salient axial lump which, after assembly, sits close to a hub of the impeller.

2. The apparatus as claimed in claim 1, wherein the walls of the housing and of the volute delimiting said duct have rounded shapes to give the duct a substantially smooth and uniform configuration without salient or re-entrant sharp corners.

3. The apparatus as claimed in claim 1, wherein the gas inlet orifice extends over an entire periphery of the motor.

4. The apparatus as claimed in claim 1, wherein the housing is flared in a manner of a bell of a trumpet at the gas inlet orifice into said air feed duct.

5. The apparatus as claimed in claim 2, wherein the gas inlet orifice extends over an entire periphery of the motor.

6. The apparatus as claimed in claim 2, wherein the housing is flared in a manner of a bell of a trumpet at the gas inlet orifice into said air feed duct.

7. The apparatus as claimed in claim 3, wherein the housing is flared in a manner of a bell of a trumpet at the gas inlet orifice into said air feed duct.

8. The apparatus as claimed in claim 5, wherein the housing is flared in a manner of a bell of a trumpet at the gas inlet orifice into said air feed duct.

9. The apparatus as claimed in claim 1, wherein the apparatus is a respiratory assistance apparatus.

10. The apparatus as claimed in claim 2, wherein the substantially smooth and uniform configuration without salient or re-entrant sharp corners includes a base of the volute and at the salient axial lump of the housing.

11. An respiratory assistance apparatus, comprising:
a housing;
an air feed duct delimited by the housing;
a volute, the volute having an inlet opening which is in communication with the air feed duct;
an impeller situated immediately downstream of the inlet opening of the volute, the impeller comprising an impeller inlet opening connected to the inlet opening of the volute and outlet orifices opening into the volute; and
a motor configured for driving a rotation of the impeller so as to generate a centrifugal air flow in the volute, wherein:
the housing has a first part with a wall configured for, after assembly, to extend around the motor, espousing a shape of the motor in such a way as to lie at a substantially constant distance from the motor, the housing and the motor between them delimiting a gas flow passage with a gas inlet orifice at an end opposite to the impeller;
the housing has a second part with a wall configured for, after assembly, to extend around the volute, espousing a shape of the volute so as to lie at a substantially constant distance from the volute, the housing and the volute between them delimiting a gas flow passage extending as far as the inlet opening of the volute; and
the housing internally forms a salient axial lump which, after assembly, sits close to a hub of the impeller.

12. The respiratory assistance apparatus as claimed in claim 11, wherein the walls of the housing and of the volute delimiting said duct have rounded shapes to give the duct a substantially smooth and uniform configuration without salient or re-entrant sharp corners.

13. The respiratory assistance apparatus as claimed in claim 11, wherein the gas inlet orifice extends over an entire periphery of the motor.

14. The respiratory assistance apparatus as claimed in claim 11, wherein the housing is flared in a manner of a bell of a trumpet at the gas inlet orifice into said air feed duct.

15. The respiratory assistance apparatus as claimed in claim 12, wherein the gas inlet orifice extends over an entire periphery of the motor.

16. The respiratory assistance apparatus as claimed in claim 12, wherein the housing is flared in a manner of a bell of a trumpet at the gas inlet orifice into said air feed duct.

17. The respiratory assistance apparatus as claimed in claim 13, wherein the housing is flared in a manner of a bell of a trumpet at the gas inlet orifice into said air feed duct.

18. The respiratory assistance apparatus as claimed in claim 15, wherein the housing is flared in a manner of a bell of a trumpet at the gas inlet orifice into said air feed duct.

19. The respiratory assistance apparatus as claimed in claim 12, wherein the substantially smooth and uniform configuration without salient or re-entrant sharp corners includes a base of the volute and at the salient axial lump of the housing.

* * * * *